US005507300A

United States Patent [19]
Mukai et al.

[11] Patent Number: 5,507,300
[45] Date of Patent: Apr. 16, 1996

[54] GUIDE WIRE FEEDING DEVICE

[75] Inventors: Shoso Mukai; Hiroaki Tuchiya, both of Shizuoka, Japan

[73] Assignee: Sherwood Medical Company, St. Louis, Mo.

[21] Appl. No.: 316,144

[22] Filed: Sep. 30, 1994

[30] Foreign Application Priority Data

Oct. 6, 1993 [JP] Japan ..................... 5-54323

[51] Int. Cl.$^6$ ..................................... A61B 5/00
[52] U.S. Cl. ........................................... 128/772
[58] Field of Search .................... 128/657, 658, 128/772; 604/158, 159, 164, 165

[56] References Cited

U.S. PATENT DOCUMENTS

| | | | |
|---|---|---|---|
| 3,561,445 | 2/1971 | Katerndahl et al. | 128/214.4 |
| 4,425,908 | 1/1984 | Simon | 128/1 R |
| 4,860,757 | 8/1989 | Lynch et al. | 128/657 |
| 4,957,117 | 9/1990 | Wysham | 128/772 |
| 5,125,906 | 6/1992 | Fleck | 604/171 |
| 5,161,534 | 11/1992 | Berthiaume | 128/657 |
| 5,282,479 | 2/1994 | Havran | 128/772 |
| 5,312,338 | 5/1994 | Nelson et al. | 128/657 |
| 5,325,746 | 7/1994 | Anderson | 128/657 |
| 5,328,868 | 7/1994 | Kimmelstiel | 128/772 |
| 5,366,444 | 11/1994 | Martin | 604/159 |
| 5,392,778 | 2/1995 | Horzewski | 128/657 |

FOREIGN PATENT DOCUMENTS 2056919 6/1993 Canada.

*Primary Examiner*—Max Hindenburg
*Attorney, Agent, or Firm*—Montgomery W. Smith; Rita D. Vacca

[57] ABSTRACT

A guide wire feeding device for operation by a single hand of a physician is disclosed. The device includes an elastic locking ring which allows the guide wire to be fixed in relative position with the feeding device if desired.

4 Claims, 3 Drawing Sheets

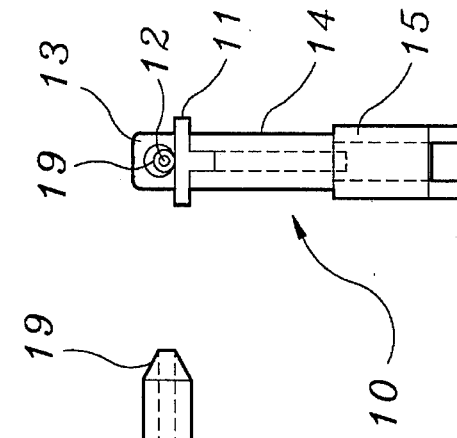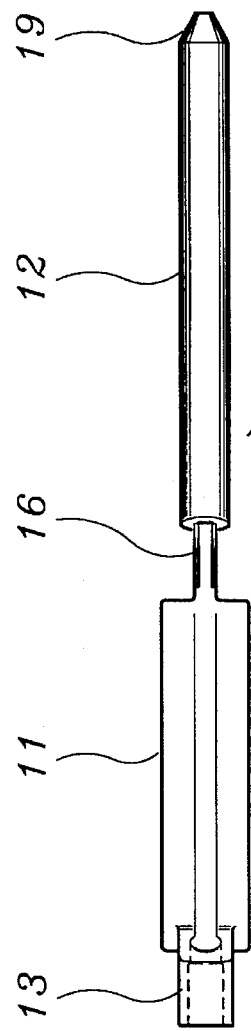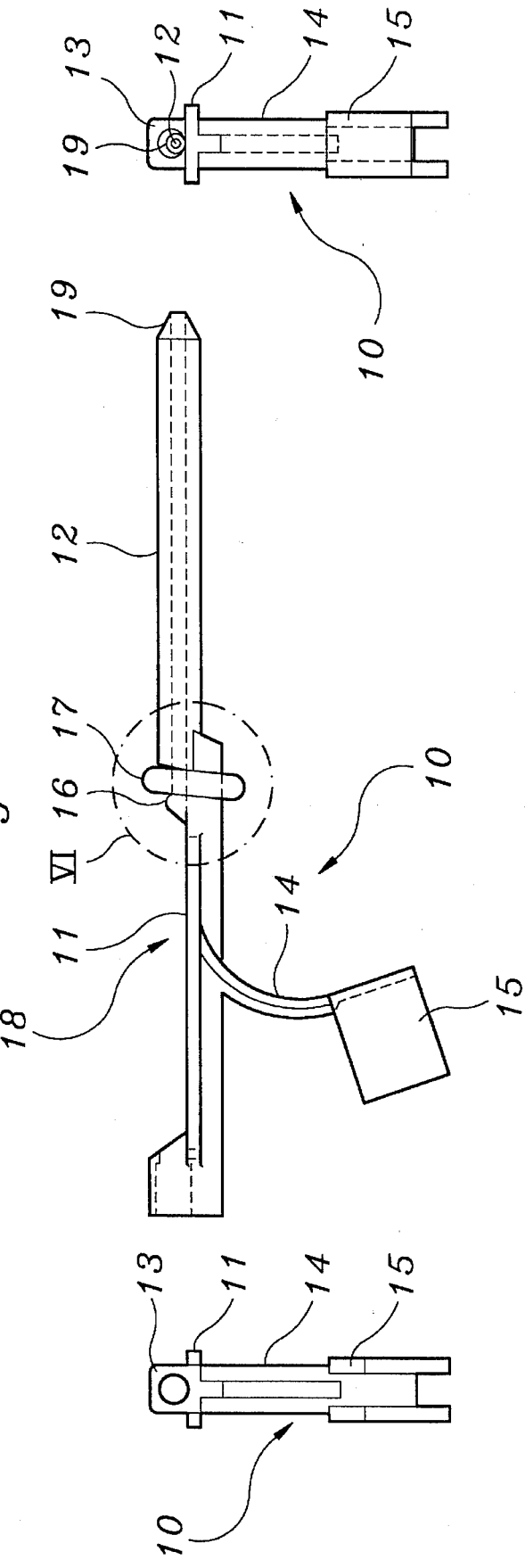
Figure 5
Figure 3
Figure 2
Figure 4

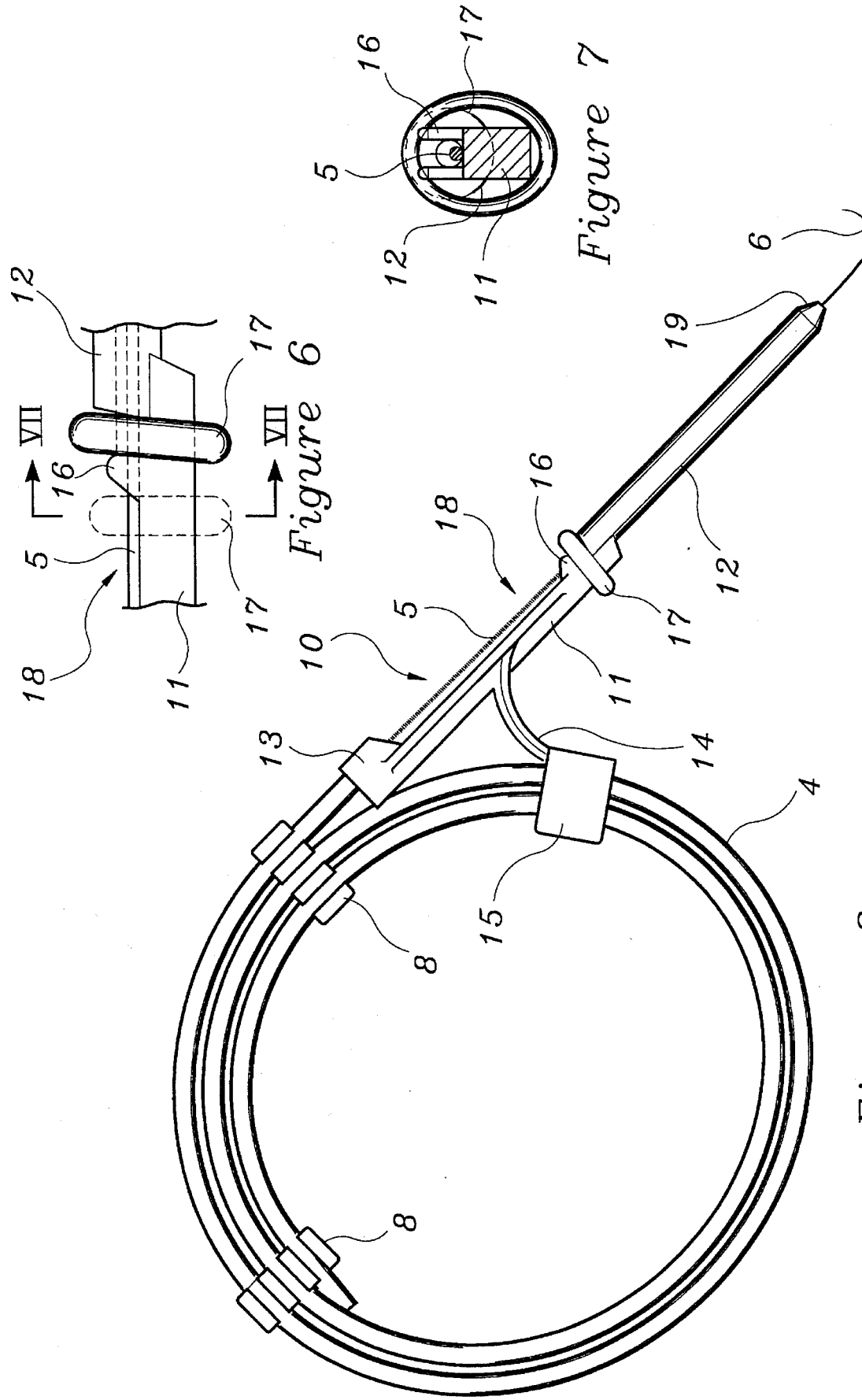

GUIDE WIRE FEEDING DEVICE

BACKGROUND OF THE INVENTION

1. Field of the Invention

The present invention relates to a device for single handed manipulation of a guide wire. More specifically, the present invention relates to a device for feeding a guide wire through a catheter, cannula or needle into a body cavity of a patient.

2. Prior Art

Guide wires are commonly inserted through a catheter, cannula or needle into a body cavity, such as a blood vessel, of a patient. The guide wire is positioned to allow a catheter to be passed therealong to follow the path of the guide wire into the patient. The guide wire is thereafter withdrawn and the catheter is ready for further positioning and use.

As shown in the prior art guide wire assembly of FIG. 1, a straightener 1, which includes a conically-shaped connector portion 2 and a smaller diameter portion 3, is formed with an interior lumen through which a guide wire 5 must pass as it is extracted from its flexible storage tube 4. The flexible storage tube 4 can be disposed in the shape of a curve, or a series of loops, as depicted in FIG. 1 to facilitate ease of manipulation. A series of retainers 8 can be used to hold the storage tube 4 in its looped configuration. The guide wire 5 is preferably of a standard coiled spring design and slidably positioned within the storage tube 4 in a sterile condition. The distal end of the guide wire 5 is also often preferably formed in the shape of a flexible "J" 6, which may be straightened by pulling the distal end of the guide wire 5 into the straightening element 1 to which it must conform. The straightening element 1 is attached to the tube 4 at the distal end 9 thereof by inserting the small diameter portion 3 of the straightener 1 thereinto. The small diameter portion 3 is sized to cause a snug fit with the distal end 9 of the tube 4.

The guide wire 5 is inserted into a vein or artery of a patient through a catheter 7, or a cannula or needle as is well known in the art.

Prior art guide wire insertion systems as described above are often very difficult to manipulate, and often allow exposure of the guide wire to a non-sterile environment during the insertion procedure. Commonly, a guide wire such as described in the prior art FIG. 1 is completely removed from its flexible storage tube prior to insertion, and is wound in the physician's hand and inserted through the needle or catheter into the patient's blood vessel or other body cavity. This procedure often necessitates the involvement of more than one physician since three hands can be required to hold the needle or cannula stationary while the guide wire is pulled through the straightener then pushed through the needle or cannula. Further, extension and manipulation of the guide wire after removal from its flexible storage tube and prior to its insertion can lead to contamination.

U.S. Pat. No. 5,125,906 issued to Fleck attempts to solve the above-described prior art problems by providing a hand held device for feeding a guide wire from its flexible storage tube into a needle or cannula. The Fleck device comprises a longitudinal member having a rear connection element for connecting to the flexible storage tube and a distally mounted straightener for straightening the guide wire as it passes through the device. A centrally positioned section of the device provides thumb and forefinger access to the guide wire, enabling the physician to advance the guide wire directly from its storage tube into the needle or cannula with a single hand.

The Fleck device, although an improvement in the art of guide wire manipulation, nevertheless fails to address several specific problems. Most importantly, when using the Fleck device, it is necessary for the physician to continuously hold the device with a thumb or finger placed directly against the guide wire at the central open section thereof in order to ensure that no inadvertent movement of the guide wire relative to the device occurs. Also, should the physician release the device to perform some other procedure, the guide wire is allowed free movement relative to the device which can cause exposure of the guide wire to contamination and/or misplacement of the guide wire in the body cavity thereto. Finally, the physician must maintain sufficient pressure against the guide wire in the device at all times to ensure that intentional movement of the device for proper placement of the guide wire is also accompanied by identical movement of the guide wire.

It would be desirable therefor for the physician to be able to ensure that the guide wire is held in position in the feeding device whenever it is desired to manipulate the feeding device and guide wire together, or whenever it is necessary to let go of the feeding device to perform another procedure.

OBJECTS AND SUMMARY OF THE INVENTION

A principal object of the present invention is to provide a guide wire feeding device which is capable of holding a guide wire in a fixed position relative thereto whenever so desired by the physician.

The presently preferred embodiment of the invention includes a guide wire feeding device having a longitudinal base member which can be attached to the flexible storage tube of a guide wire and which includes an elongate straightening barrel at the distal end thereof for receiving and straightening the guide wire as it is fed from its storage tube into a catheter or cannula by manipulation of the guide wire by the physician's fingers as the guide wire passes through a central portion of the longitudinal base member. The longitudinal base member is attached to a handle which includes a U-shaped clamp thereon for securing the device to the guide wire storage tube. The invention also includes an elastic ring member which surrounds the longitudinal base member of the device and is positioned in the central section thereof and which is held away from the guide wire in a first, non-locking position by a pair of elevated stopping shoulders, but which can be manipulated by the physician's thumb or forefinger to a second, locking position wherein the elastic ring member securely holds the guide wire against the longitudinal base member and prevents relative movement thereof with respect to the device until the physician again manipulates the elastic ring member back to its first position over the stopping shoulders. The disclosed device is designed to allow the operator to easily lock the guide wire in position relative to the device whenever the physician desires to ensure that manipulation of the device will also identically manipulate the guide wire, or whenever the surgeon must release the device to perform other procedures.

The above and other objects and advantages of the present invention will become apparent from the following more detailed description, when taken in conjunction with the accompanying drawings in which like elements are identified with like numerals throughout.

BRIEF DESCRIPTION OF THE DRAWINGS

FIG. 2 is a side view of a guide wire feeding device formed in accordance with the principals of the present invention;

FIG. 3 is a top view of the guide wire feeding device of the present invention;

FIG. 4 is a rear view of the guide wire feeding device of the present invention;

FIG. 5 is a front view of the guide wire feeding device of the present invention;

FIG. 6 is an enlarged view of a portion of the guide wire feeding device of the present invention shown in the circular area VI of FIG. 2;

FIG. 7 is a cross-sectional view of the guide wire feeding device of the present invention taken along line VII—VII of FIG. 6; and FIG. 8 shows the guide wire feeding device of the present invention attached to a guide wire and storage tube for use.

DETAILED DESCRIPTION OF THE PREFERRED EMBODIMENT

Figure 1:
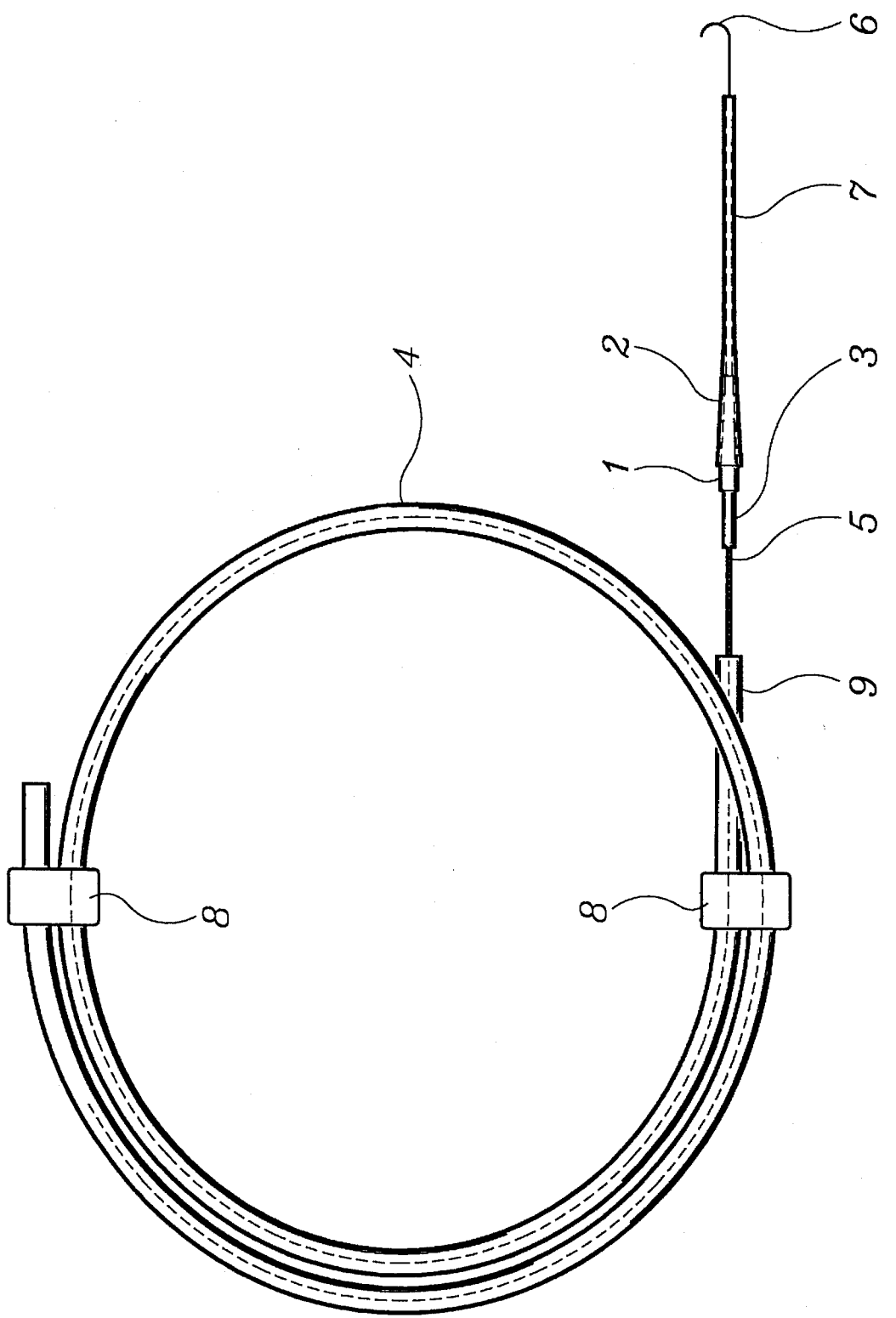
FIG. 1 shows a plan view of a prior art guide wire positioned in a flexible storage tube in preparation for use.

As shown in the exemplary drawings for the purpose of illustration, a preferred embodiment of a guide wire feeding device made in accordance with the principals of the present invention, referred to generally by the reference numeral 10 is provided for single handed manipulation of a guide wire during its insertion into the body cavity of a patient, and for locking of the guide wire in fixed position relative to the device when desired.

More specifically, as shown in FIG. 2, the guide wire feeding device 10 comprises a longitudinal base member 11 which includes a straightening barrel 12 positioned at the distal end thereof and a storage tube attachment member 13 positioned at the proximal end thereof. The barrel 12 and attachment member 13 are separated by an open central section 18 in which the guide wire 5 is exposed as it passes through the longitudinal base member 11 (see FIG. 8).

The straightening barrel member 12 includes an axial bore therethrough which is sized to permit passage of the guide wire 5 in a snug manner to force it to be straightened as it is fed therethrough. Preferably, the barrel member 12 includes a tapered distal end portion 19 which facilitates its connection to a needle or cannula through which the guide wire is intended to be fed.

The device 10 further includes an arced handle member 14 which is attached to the underside of the longitudinal base member 11, and which is preferably sized to allow a physician to grip the device 10 by the last three fingers of the hand during use. The base of the arced handle member 14 is formed into a U-shaped clamp 15 which can be attached to the flexible storage tube 4 (as best shown in FIG. 8).

As shown in FIGS. 6 and 7, the open central section 18 includes a pair of elevated stopping shoulders 16 which are positioned directly adjacent the barrel member 12. Further, an elastic ring member 17 is positioned around the longitudinal base member 11 directly adjacent the stopping shoulders 16.

Referring specifically to FIG. 6, the elastic ring member 17 can be manipulated by the thumb or forefinger of the physician between a non-locking position in which it is held between the barrel member 12 and the elevated stopping shoulders 16, and a locking position (shown in dashed lines) in which the ring member 17 is moved away from the elevated portion of the stopping shoulders 16 and allowed to compress against a portion of the guide wire 5 positioned in the open central section 18.

FIG. 8 shows the guide wire feeding device 10 of the present invention as it is properly attached to the flexible storage tube 4 for use. The storage tube attachment member 13 is attached directly to the open end 9 of the storage tube 4, and the guide wire 5 passes completely along the longitudinal base member 11, past the open central section 18, and through the straightening barrel member 12. The flexible storage tube 4 is coiled into a series of loops which are held in their looped orientation by the retainers 8 and the U-shaped clamp 15.

In operation, the guide wire feeding device 10 of the present invention is attached to the flexible storage tube 4 and the guide wire 5 is passed therethrough as shown. The physician then holds the device 10 in a single hand with the last three fingers of the hand curled about the arced handle member 14 and the thumb and index finger positioned about the longitudinal base member 11 in such a manner that the thumb can contact the portion of the guide wire 5 positioned in the open central section 18 of the longitudinal base member 11. The physician then manipulates the guide wire 5 to advance or retract the guide wire 5 as desired to properly position the guide wire 5 in the desired location within a body cavity of the patient. If at any time however, the surgeon wishes to either release the device 10, or manipulate the guide wire 5 by manipulation of the device 10 without the necessity of maintaining contact at the guide wire 5 with the thumb, the physician merely extends the thumb and/or forefinger over the elastic ring member 17 and draws it in a rearward direction over the elevated stopping shoulder 16 and into the open central section 18. When positioned in this manner, the elastic ring member 17 compresses the guide wire 5 against the longitudinal base member 11 and prevents relative movement thereof with respect to the device 10. Manipulation of the device 10 thereafter simultaneously manipulates the guide wire 5. Alternatively, the physician can thereafter release the device 10 and be assured that no movement of the guide wire 5 relative to the device 10 will occur.

When the physician wishes to resume manipulation of the guide wire 5 relative to the device 10, the physician merely uses the thumb and/or forefinger to force the elastic ring member 17 forward over the elevated stopping shoulders 16 until it comes to rest between the stopping shoulders 16 and the distal end of the barrel member 12. In this position, the elastic ring member 17 is stretched to a diameter which prevents it from contacting the guide wire 5. Therefore, the guide wire 5 is allowed to move freely relative to the device 10.

It should be understood from the foregoing that, while a particular embodiment of the present invention has been illustrated and described, various modifications can be made thereto without departing from the spirit and scope of the invention. Accordingly, it is not intended that the invention be limited except as by the appended claims.

We claim:

1. A hand held guide wire feeding device for feeding a guide wire from a flexible guide wire storage tube into a body cavity of a patient, said device comprising:

a longitudinal base member having a storage tube attachment member formed at a proximal end thereof which is attachable to the flexible guide wire storage tube, a straightening barrel member formed at a distal end of said longitudinal base member, and an open central section positioned between said storage tube attachment member and said straightening barrel member;

at least one elevated stopping shoulder located in said open central section of said longitudinal base member; and an elastic ring member positioned around said longitudinal base member at said open central section thereof;

whereby, said elastic ring member can be moved from a first position relative to said at least one elevated stopping shoulder to a second position relative to said at least one elevated stopping shoulder and wherein a guide wire passing along said longitudinal base member is free to move relative thereto when said elastic ring member is in said first position, and is compressed against said longitudinal base member when said elastic ring member is in said second position.

2. The hand held guide wire feeding device of claim 1 wherein said elastic ring member contacts a portion of said straightening barrel member when in said first position.

3. The hand held guide wire feeding device of claim 1 further including a handle member attached to said longitudinal base member.

4. The hand held guide wire feeding device of claim 3 wherein said handle further includes a clamp for attachment to the flexible storage tube of the guide wire.

* * * * *